US012778264B2

(12) United States Patent
Zhou et al.

(10) Patent No.: US 12,778,264 B2
(45) Date of Patent: Nov. 3, 2026

(54) APPLICATOR

(71) Applicant: SHYA HSIN PACKAGING INDUSTRY (CHINA) CO., LTD., Kunshan (CN)

(72) Inventors: Mini Zhou, Kunshan (CN); Weijin Chen, Kunshan (CN)

(73) Assignee: SHYA HSIN PACKAGING INDUSTRY (CHINA) CO., LTD., Kunshan (CN)

( * ) Notice: Subject to any disclaimer, the term of this patent is extended or adjusted under 35 U.S.C. 154(b) by 315 days.

(21) Appl. No.: 18/422,023

(22) Filed: Jan. 25, 2024

(65) Prior Publication Data

US 2025/0134234 A1 May 1, 2025

(30) Foreign Application Priority Data

Oct. 30, 2023 (CN) ......................... 202311422252.9

(51) Int. Cl.
*A45D 34/04* (2006.01)
*A61M 35/00* (2006.01)

(52) U.S. Cl.
CPC ......... *A45D 34/042* (2013.01); *A61M 35/003* (2013.01); *A45D 2200/10* (2013.01); *A61M 2210/0625* (2013.01)

(58) Field of Classification Search
CPC ............. A45D 34/042; A45D 2200/10; A61M 35/003; A61M 2210/0625; A61M 35/006
See application file for complete search history.

(56) References Cited

U.S. PATENT DOCUMENTS

| | | | | |
|---|---|---|---|---|
| 5,899,622 | A * | 5/1999 | Gueret | A45D 34/045 401/122 |
| 2017/0347776 | A1 | 12/2017 | Jacob | |
| 2019/0008262 | A1 | 1/2019 | Hervet | |
| 2020/0069033 | A1 * | 3/2020 | Park | A46D 1/02 |
| 2020/0237074 | A1 * | 7/2020 | Gauttier | B29C 44/42 |
| 2023/0008001 | A1 | 1/2023 | Park | |
| 2023/0270242 | A1 | 8/2023 | Yu | |

FOREIGN PATENT DOCUMENTS

| | | | |
|---|---|---|---|
| WO | 2014174423 | A1 | 10/2014 |
| WO | 2023275581 | A1 | 1/2023 |

* cited by examiner

*Primary Examiner* — Susan S Su
*Assistant Examiner* — Erin A Kim
(74) *Attorney, Agent, or Firm* — Bayramoglu Law Offices LLC

(57) ABSTRACT

An applicator is configured to apply a cosmetic, a skin care product and/or a medicine to a hairless skin, and includes a mounting portion and an application portion fixedly connected to the mounting portion, where at least two flocks are provided on the application portion; the mounting portion, the application portion and the flocks are an integrally injection-molded piece made of a thermoplastic material; and a shore hardness of the thermoplastic material is greater than 65 A. Since the mounting portion, the application portion and the flocks are integrally formed by injection molding, the applicator omits the conventional flocking process to prevent flock falling and dissolution of a glue in a cosmetic material.

16 Claims, 7 Drawing Sheets

APPLICATOR

CROSS REFERENCE TO THE RELATED APPLICATIONS

This application is based upon and claims priority to Chinese Patent Application No. 202311422252.9, filed on Oct. 30, 2023, the entire contents of which are incorporated herein by reference.

TECHNICAL FIELD

The present disclosure relates to a cosmetic application technology, and in particular to an applicator.

BACKGROUND

Cosmetics such as a lip glaze are usually applied to a lip through a cotton head in the prior art. Specifically, the cotton head is manufactured by performing injection molding to obtain the plastic body, coating a glue to the body, and allowing the glue coated body to fully adsorb flocks by means of electrostatic flocking, so as to obtain the cotton head including a plastic member body and a flock layer outer surface.

However, due to the glue, the existing cotton head has the following shortages: the glue is prone to a failure, such that the flocks may fall off, or the glue may be dissolved in the cosmetic material to affect both quality of the cosmetic and a health of the user.

SUMMARY

The present disclosure provides an applicator to overcome the above defects. Since a mounting portion, an application portion and flocks are integrally formed by injection molding, the applicator omits the conventional flocking process to prevent flock falling and dissolution of a glue in a cosmetic material.

To solve the technical problems, the present disclosure employs the following technical solutions.

The present disclosure provides an applicator, configured to apply a cosmetic, a skin care product and/or a medicine to a hairless skin, and including a mounting portion and an application portion fixedly connected to the mounting portion, where at least two flocks are provided on the application portion; the mounting portion, the application portion and the flocks are an integrally injection-molded piece made of a thermoplastic material; and a shore hardness of the thermoplastic material is greater than 65 A.

Optionally, the shore hardness of the thermoplastic material is 70 A to 95 A.

Optionally, the shore hardness of the thermoplastic material is 70 A, 72 A, 75 A, 80 A, 85 A, 87 A or 90 A.

Optionally, a first end of the flock is fixedly connected to the application portion, and a second end of the flock is a free end; the second end of the flock extends toward an outer side of the application portion; the flock has an average diameter of 0.06 mm to 0.2 mm; and the flock has a length L of 0.6 mm to 2 mm.

Optionally, a distance H between two adjacent flocks is identical.

Optionally, a distance H between two adjacent flocks is 0.1 mm to 0.6 mm.

Optionally, a density of the flocks on the application portion is 2 pieces/mm$^2$ to 30 pieces/mm$^2$.

Optionally, the flock is spatially shaped as a designated cone; the designated cone is a circular cone or a truncated cone; and the designated cone has a conicity of 1:15 to 1:20.

Optionally, the thermoplastic material includes the following components in parts by weight: 20-40 parts of polyurethane (PU), 20-30 parts of a polyester fiber, 20-30 parts of a filler, 15-25 parts of a plasticizer, 0-5 parts of a colorant, 0-1 parts of an ultraviolet stabilizer, and 0-1 parts of an antioxidant.

Optionally, the thermoplastic material includes the following components in parts by weight: 15-30 parts of a styrene-ethylene-butylene-styrene block copolymer (SEBS), 20-40 parts of a paraffin oil, 15-30 parts of polypropylene, 15-30 parts of calcium carbonate, and 0-3 parts of an auxiliary material.

Optionally, the thermoplastic material includes the following components in parts by weight: 95-99.5 parts of 1,4-Benzenedicarboxylic acid dimethyl ester polymer with 1,4-butanediol and α-hydro-ω-hydroxypoly(oxy-1,4-butanediyl), and 0.5-2 parts of an adhesive.

Optionally, the thermoplastic material includes the following components in parts by weight: 95-99.8 parts of a polymer of diphenyl isophthalate, 1,4-butanediol, terephthalic acid and poly(1,4-butanediol), and 0.1-2 parts of an adhesive.

The present disclosure has the following beneficial effects: The applicator is the integrally injection-molded piece made of the thermoplastic material, namely the mounting portion, the application portion and the flocks are formed at the same time. Compared with a conventional brush head process, the applicator omits a flocking process, simplifies a production process, improves a production efficiency and lowers a manufacturing cost. Without glue coating, the applicator prevents flock falling and dissolution of a glue in a cosmetic material. The shore hardness of the thermoplastic material is 65 A or more. Compared with conventional flocks, the hardness of the flocks is improved, and a protective gap between the flocks has better performance correspondingly. Therefore, the applicator has a better loading capability at a single time, and meets a scenario with a large application amount and a high loading requirement.

Figure 1:
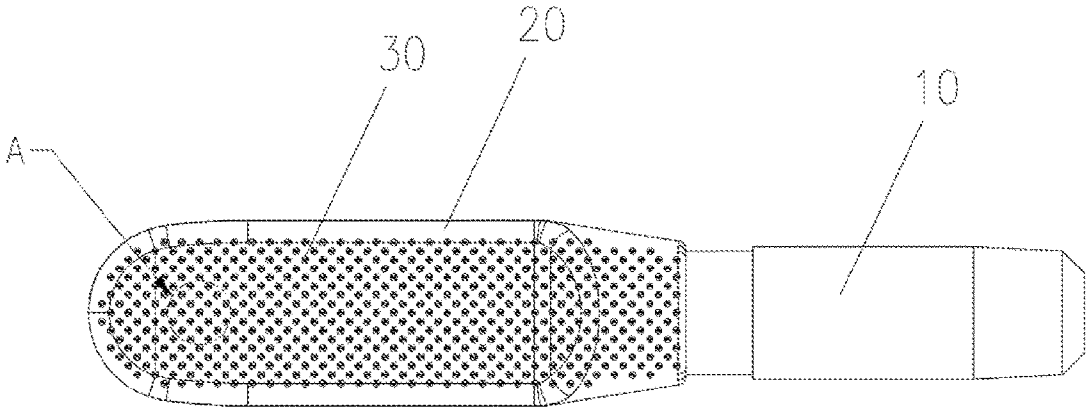
FIG. 1 is a front view of an applicator according to the present disclosure.

In the figures: 10—mounting portion, 20—application portion, 21—first surface, 22—second surface, and 30—flock.

DETAILED DESCRIPTION OF THE EMBODIMENTS

The following describes the technical solutions in the embodiments of the present disclosure clearly and completely with reference to the embodiments of the present disclosure. Apparently, the embodiments described are merely some rather than all of the embodiments of the present disclosure. All other embodiments obtained by a person of ordinary skill in the art based on the embodiments of the present disclosure without creative efforts shall fall within the protection scope of the present disclosure.

It should be noted that the terms "first", "second", and so on in the description and claims of the present disclosure and in the following accompanying drawings are intended to distinguish similar objects but do not necessarily indicate a specific order or sequence. It should be understood that the objects used in such a way may be exchanged under proper conditions to make it possible to implement the described implementations of this application in sequences except those illustrated or described herein. Moreover, the terms "include", "have" and their variants mean to cover a non-exclusive inclusion. For example, a process, method, system, product or device that includes a list of steps or units is not necessarily limited to those steps or units which are clearly listed. Instead, they may include other steps or units which are not expressly listed or inherent to such a process, method, product, or device.

For ease of description, spatially relative terms, such as "above", "on the upper side of", "on the upper surface of" and "on", can be used to describe the spatial positional relationship between components or features shown in the figure. It should be understood that the spatially relative terms are intended to encompass different orientations of the components in use or operation in addition to those shown in the figure. For example, if a component in the figure is inverted, it is described as a component "above other component or structure" or "on other component or structure". Therefore, the component will be positioned as "below other component or structure" or "under other component or structure". Therefore, the exemplary term "above" may include both orientations "above" and "below". The component may also be positioned in other different ways (rotated by 90 degrees or in other orientations), but the relative description of the space should be explained accordingly.

As shown in FIGS. 1-9, an applicator is configured to apply a cosmetic, a skin care product and/or a medicine to a hairless skin, and includes mounting portion 10 and application portion 20 fixedly connected to the mounting portion 10. At least two flocks 30 are provided on the application portion 20. The mounting portion 10, the application portion 20 and the flocks 30 are an integrally injection-molded piece made of a thermoplastic material. A shore hardness of the thermoplastic material is greater than 65 A.

In the present disclosure, the applicator is the integrally injection-molded piece made of the thermoplastic material. That is, the mounting portion 10, the application portion 20 and the flocks 30 are integrally formed. Compared with a conventional brush head process, the applicator omits a flocking process, simplifies a production process, improves a production efficiency and lowers a manufacturing cost. Without glue coating, the applicator prevents flock falling and dissolution of a glue in a cosmetic material. The shore hardness of the thermoplastic material is 65 A or more. Compared with conventional flocks, the hardness of the flocks is improved, and a protective gap between the flocks has better performance correspondingly. Therefore, the applicator has a better loading capability at a single time. The present disclosure can be used to apply skin care or makeup cosmetic materials such as a lip oil, a lip gloss and a lipstick.

Optionally, the shore hardness of the thermoplastic material is 70 A to 95 A. In case of a big hardness of the flocks 30, a makeup effect will be affected. Hence, the shore hardness of the thermoplastic material is controlled at 70 A to 95 A in the present disclosure. This not only greatly improves the loading capability of the applicator at the single time, but also meets a makeup requirement of the flocks and improves a makeup comfort of the user.

Optionally, the shore hardness of the thermoplastic material is 70 A, 72 A, 75 A, 80 A, 85 A, 87 A or 90 A.

Figure 2:
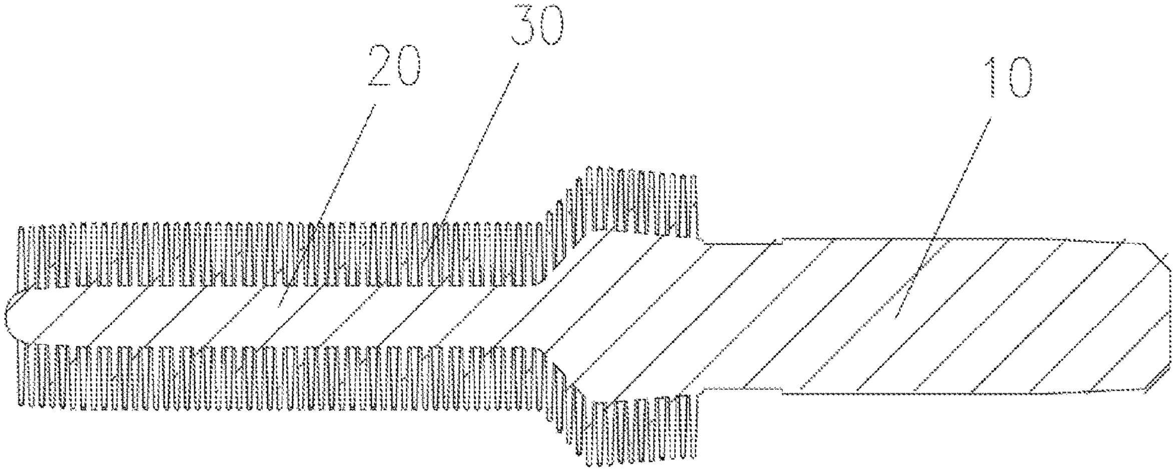
FIG. 2 is a sectional view of an applicator according to the present disclosure.
Figure 3:
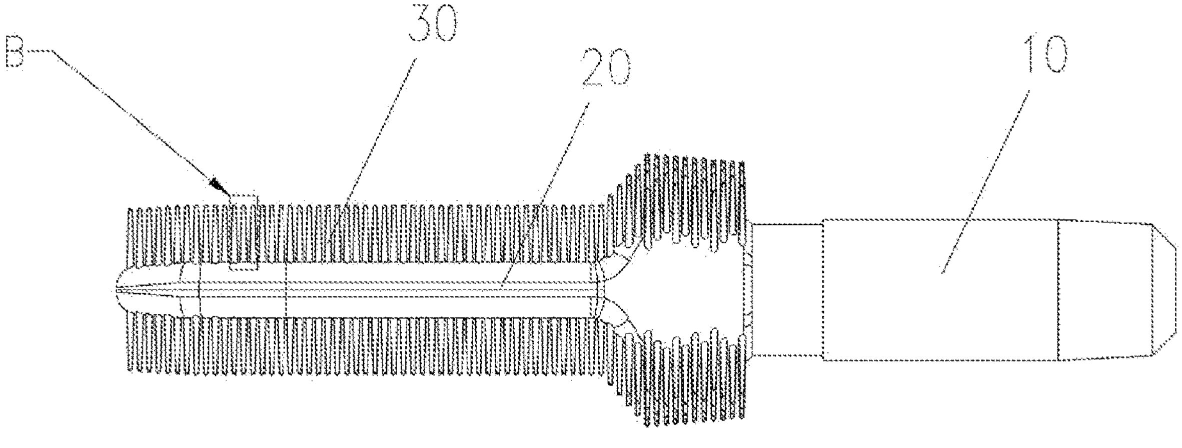
FIG. 3 is a top view of an applicator according to the present disclosure.
Figure 4:
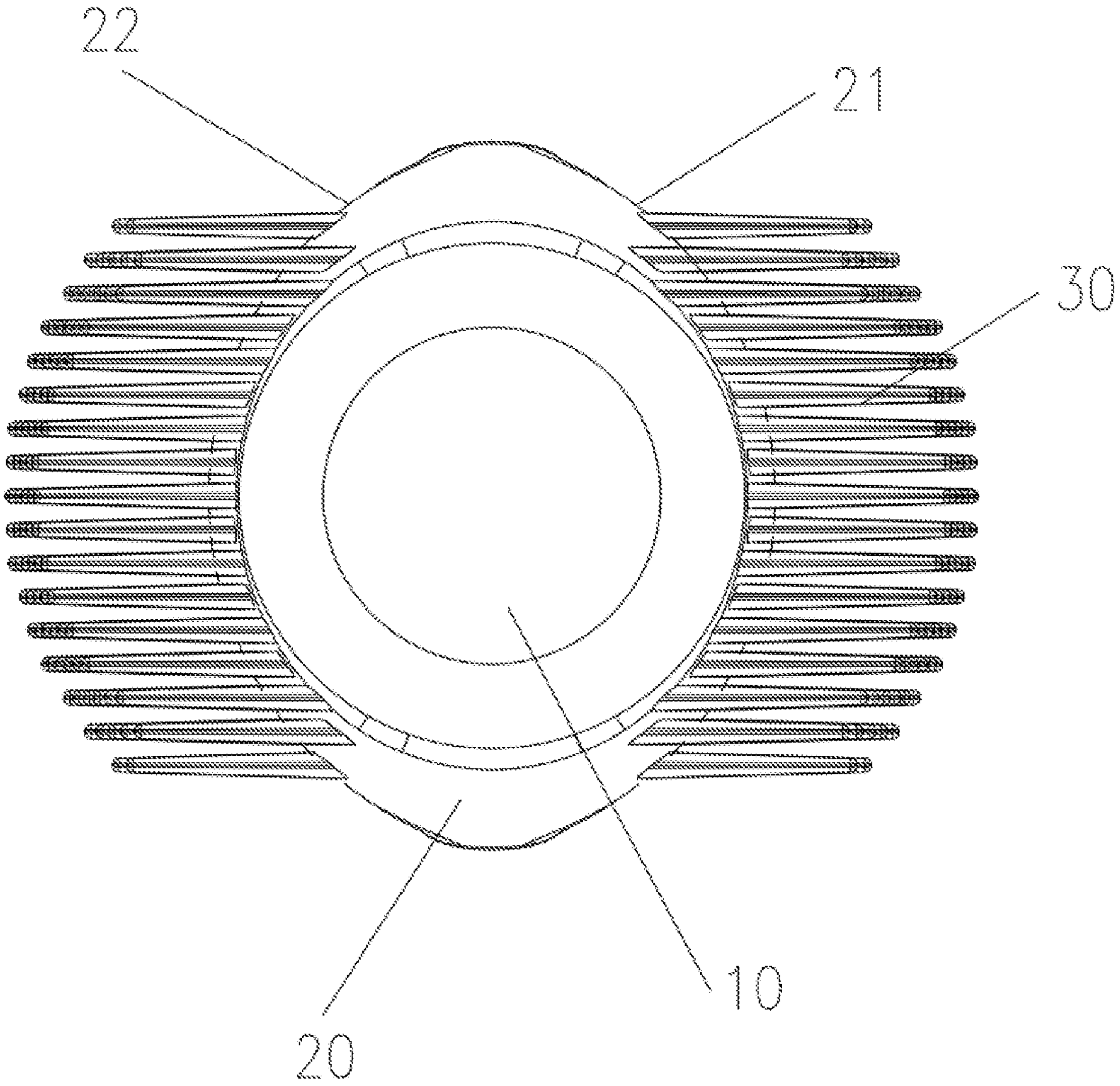
FIG. 4 is a right view of an applicator according to the present disclosure.
Figure 5:
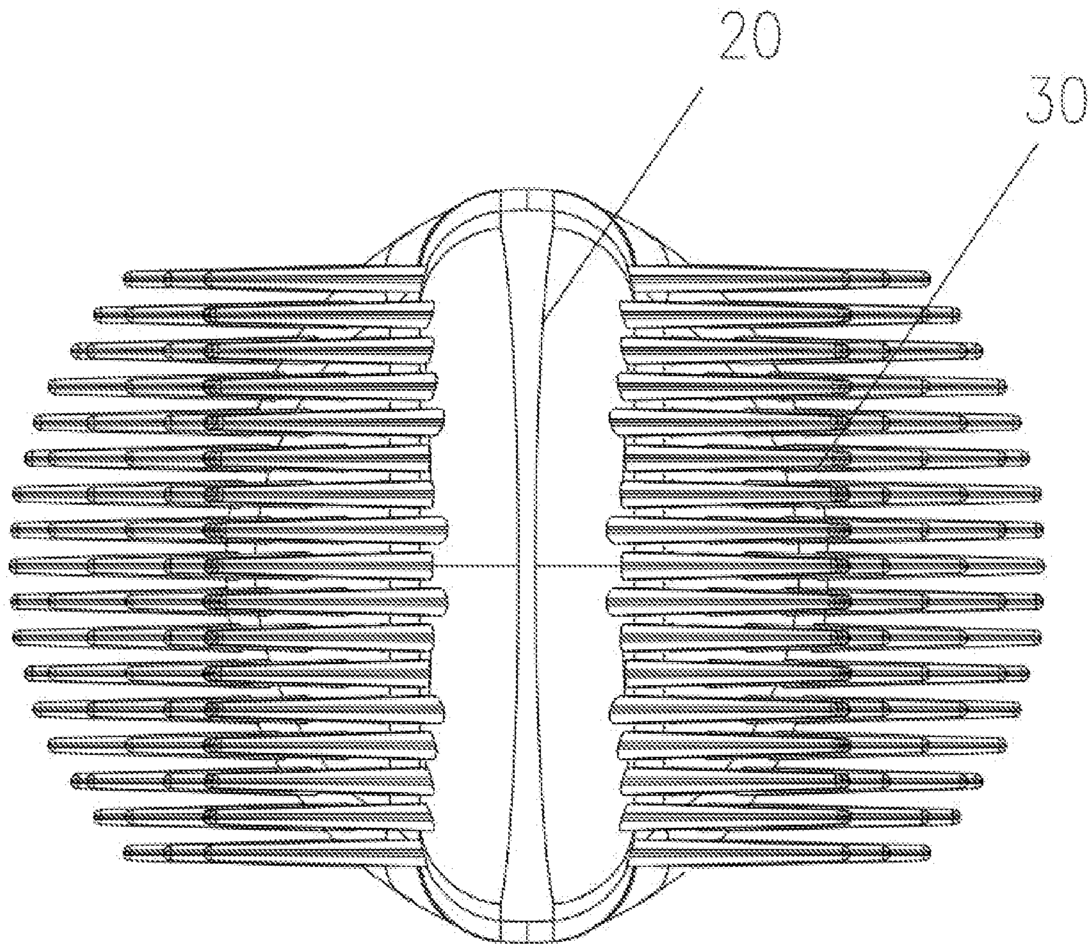
FIG. 5 is a left view of an applicator according to the present disclosure.
Figure 8:
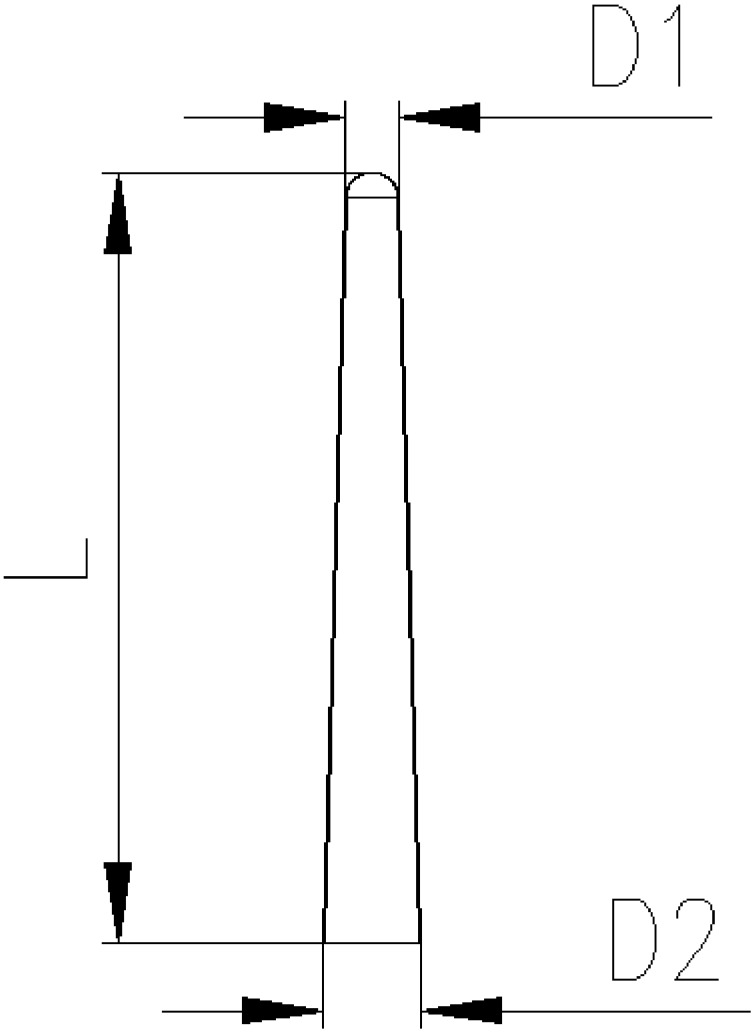
FIG. 8 is a first schematic structural view of a flock according to the present disclosure.
Figure 9:
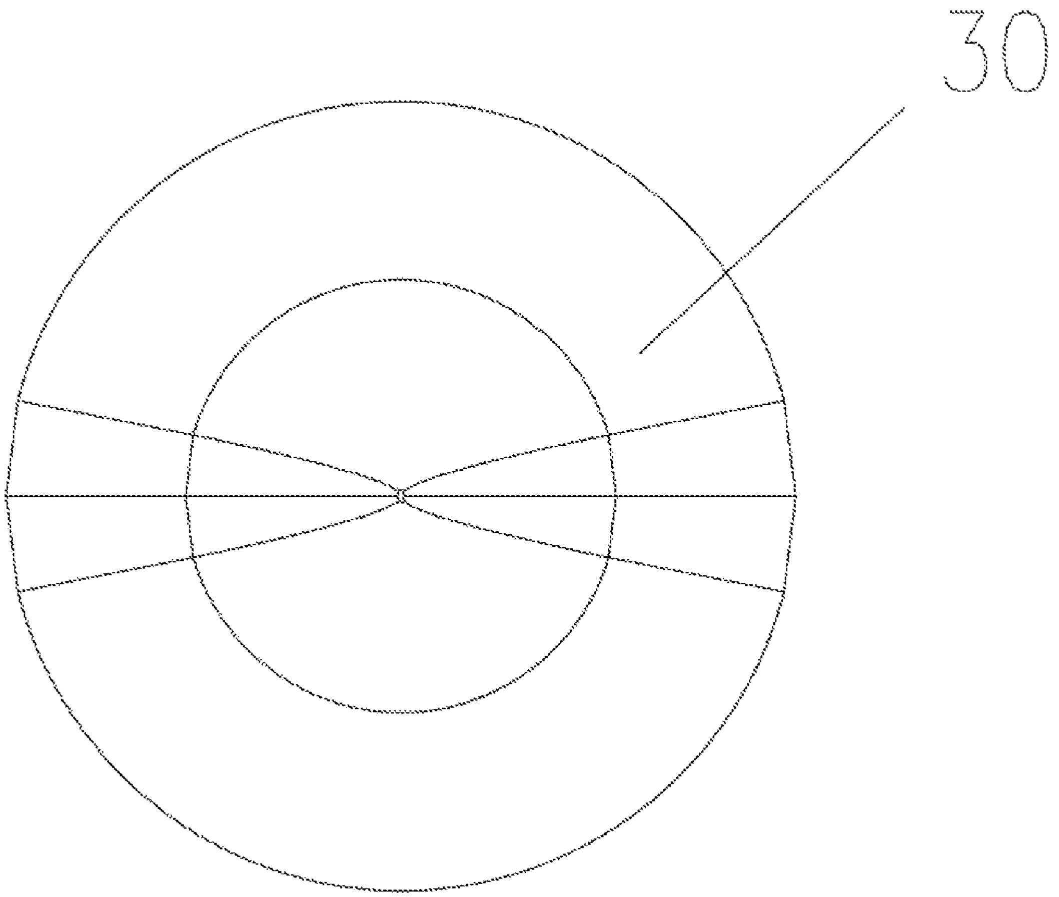
FIG. 9 is a second schematic structural view of a flock according to the present disclosure.

As shown in FIG. 2, a first end of the flock 30 is fixedly connected to the application portion 20, and a second end of the flock 30 is a free end. The second end of the flock 30 extends toward an outer side of the application portion 20. The flock 30 has an average diameter of 0.06 mm to 0.2 mm. The flock 30 has a length L of 0.6 mm to 2 mm. Optionally, the average diameter of the flock 30 is 0.08 mm to 0.12 mm. Optionally, the average diameter of the flock is 0.05 mm, 0.06 mm, 0.07 mm, 0.08 mm, 0.09 mm, 0.1 mm, 0.11 mm, and 0.12 mm. The so-called length L of the flock 30 refers to a distance from the first end to the second end of the flock 30. Optionally, as shown in FIG. 8 and FIG. 9, the length L of the flock 30 is 0.75 mm to 1.6 mm. Optionally, the length L of the flock 30 is 0.75 mm, 0.8 mm, 0.9 mm, 1.1 mm, 1.2 mm, 1.3 mm, 1.4 mm, 1.6 mm, 1.7 mm, 1.8 mm, 1.9 mm or 2 mm. The flock does not fall off in use due to the small length and the small diameter, and its application effect is more uniform. In cosmetic application, the flock is soft and does not stick the lip, thereby improving a degree of satisfaction of the user.

Optionally, the flock 30 includes a cylindrical structure, a polyhedral structure, a circular truncated cone structure, a cone structure, etc. As shown in FIG. 1-5, in a possible implementation, the whole applicator is sword-shaped. The application portion 20 is tongue-shaped. The application portion 20 includes first surface 21 and second surface 22 opposite to each other. At least one of the first surface 21 and the second surface 22 is provided with the flock 30. Optionally, both the first surface 21 and the second surface 22 are provided with the flock 30. Both the first surface 21 and the second surface 22 are a planar surface, a convex surface or a concave surface. In other possible implementations, the application portion 20 is cone-shaped, drop-shaped, spoon-shaped, etc.

In a possible implementation, a cross-sectional area of the first end of the flock 30 is the same as a cross-sectional area of the second end of the flock 30. For any two points A and B on the flock 30, a cross-sectional area of the flock 30 at the point A is the same as a cross-sectional area of the flock 30 at the point B. In another possible implementation, the cross-sectional area of the first end of the flock 30 is greater than the cross-sectional area of the second end of the flock 30. For any two points A and B on the flock 30, if a distance from the point A to the first end of the flock is less than a distance from the point B to the first end of the flock, a cross-sectional area of the flock 30 at the point A is greater than a cross-sectional area of the flock 30 at the point B.

Figure 6:
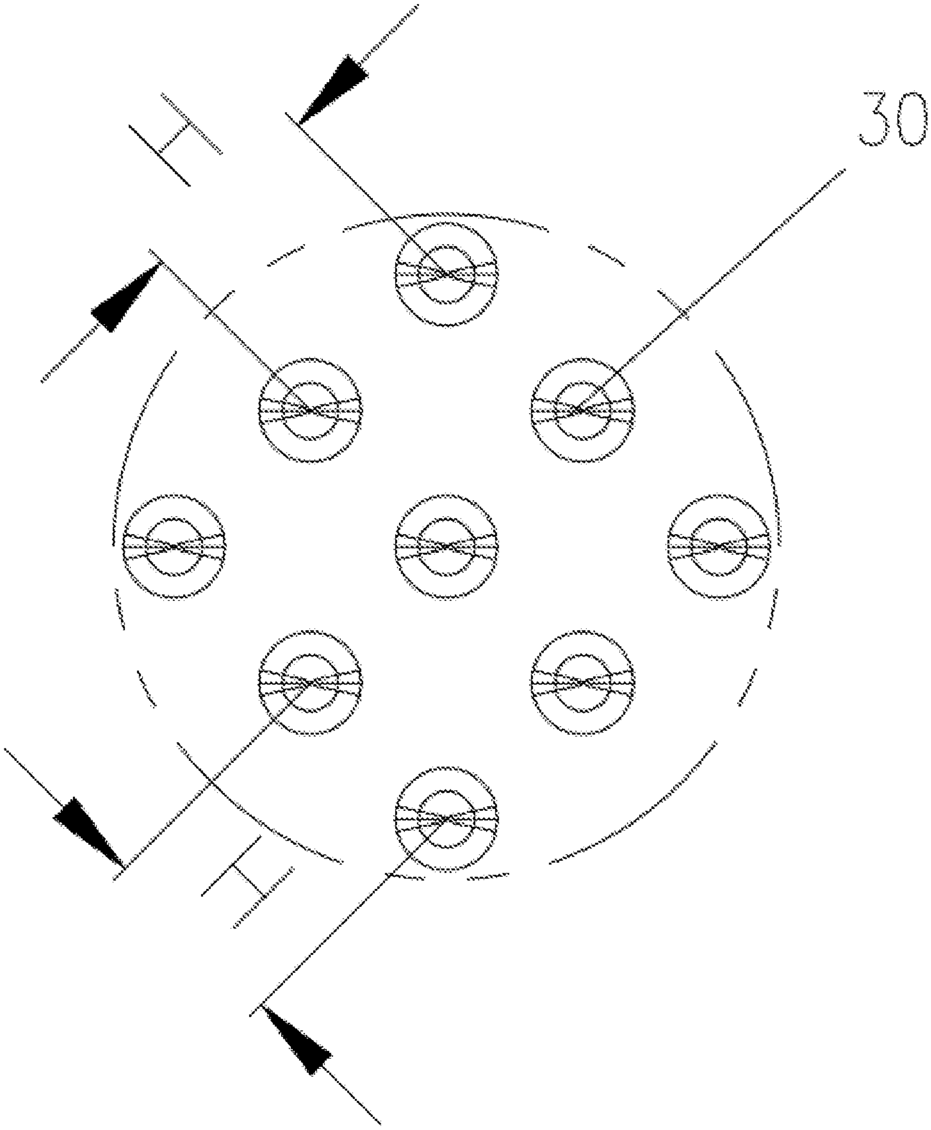
FIG. 6 is an enlarged view of A shown in FIG. 1.
Figure 7:
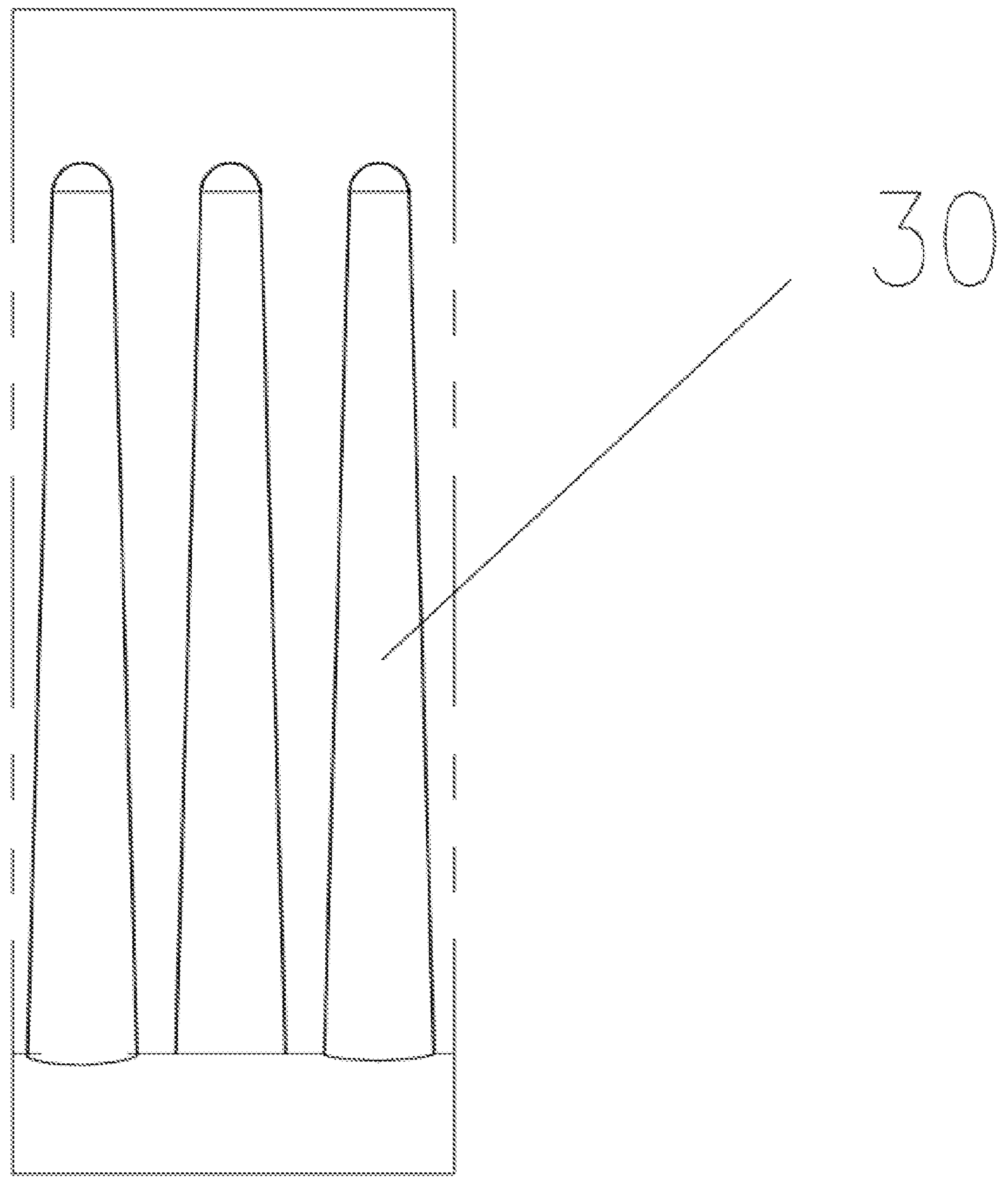
FIG. 7 is an enlarged view of B shown in FIG. 3.

In a possible implementation, a distance between two adjacent flocks 30 may not be the same. That is, the application portion 20 may be divided into different regions. There are different densities of the flocks in the different regions. In another possible implementation, a distance between two adjacent flocks 30 may also be the same. As shown in FIG. 1 and FIG. 6, a distance H between two adjacent flocks 30 is identical. That is, each region on the application portion 20 has a same density of the flocks. The so-called distance between two adjacent flocks 30 refers to a distance between central points of orthographic projections of the two adjacent flocks 30 on a surface of the application portion 20.

As shown in FIG. 6, the distance H between the two adjacent flocks 30 is 0.1 mm to 0.6 mm. Optionally, the distance between the two adjacent flocks 30 is 0.1 mm to 0.3 mm. Optionally, the distance between the two adjacent flocks 30 is 0.3 mm to 0.6 mm. Optionally, the distance H between the two adjacent flocks 30 is 0.2 mm to 0.5 mm. Optionally, the distance H between the two adjacent flocks 30 is 0.21 mm, 0.22 mm, 0.23 mm, 0.24 mm, 0.25 mm, 0.26 mm, 0.27 mm, 0.28 mm, 0.29 mm or 0.30 mm. With the appropriate distance between two adjacent flocks 30 and the appropriate hardness of the flock, the applicator has the ultra-strong loading capability at the single time.

Optionally, a density of the flocks 30 on the application portion 20 is 2 pieces/mm$^2$ to 30 pieces/mm$^2$. That is, there are 2-30 flocks 30 on each square millimeter of the application portion 20. Optionally, there are 2-15 flocks 30 on each square millimeter of the application portion 20. Optionally, there are 5-12 flocks 30 on each square millimeter of the application portion 20. Optionally, there are 10-20 flocks 30 on each square millimeter of the application portion 20. The density of the flocks on the application portion 20 is designed as required to meet different makeup requirements.

The flock 30 is spatially shaped as a designated cone. The designated cone is a circular cone or a truncated cone. The designated cone has a conicity of 1:15 to 1:20. As shown in FIG. 8, the designated cone has the conicity of (D2−D1): L. In a possible implementation, the Lis 1.2 mm, the D1 is 0.08 mm, the D2 is 0.15 mm, and the conicity is 1:17.

The thermoplastic material includes at least one of a thermoplastic polyurethane elastomer (TPU), a thermoplastic styrenic elastomer (TPES) and a thermoplastic polyester elastomer (TPEE). Optionally, the applicator is prepared with the TPU, the TPES or the TPEE. The applicator is formed through an injection mold. A plurality of recessed micro-etching holes are formed in a mold cavity. The flocks are laser etched in the sophisticated micro-level and nano-level etching holes of the mold cavity.

In some specific embodiments, the thermoplastic material of the applicator has the following types:

TPE06751: thermoplastic styrenic elastomer (TPES) produced by the DuPont in USA.

TPU1070A: thermoplastic polyurethane elastomer (TPU) produced by the Bayer in Germany.

HY5526: thermoplastic polyester elastomer (TPEE) produced by the DuPont in USA.

HY4056: thermoplastic polyester elastomer (TPEE) produced by the DuPont in USA.

HY3078: thermoplastic polyester elastomer (TPEE) produced by the DuPont in USA.

SK SKYPEL G140D: thermoplastic polyester elastomer (TPEE) produced by the SK Chemicals in Korea.

SK SKYPEL G130D: thermoplastic polyester elastomer (TPEE) produced by the SK Chemicals in Korea.

COPEC CC60CZ: thermoplastic polyurethane elastomer (TPU) produced by the Kraiburg in Germany.

In a first possible implementation, the thermoplastic material includes the following components in parts by weight: 20-40 parts of PU, 20-30 parts of a polyester fiber, 20-30 parts of a filler, 15-25 parts of a plasticizer, 0-5 parts of a colorant, 0-1 parts of an ultraviolet stabilizer, and 0-1 parts of an antioxidant. That is, the thermoplastic material is the TPU. The filler includes at least one of calcium carbonate, talcum powder, kaolin, mica, wollastonite, barium sulfate, carbon black, white carbon black, and titanium dioxide. In a specific embodiment, the TPU includes the following components in parts by weight: 35 parts of the PU, 28 parts of the polyester fiber, 25 parts of the calcium carbonate, 20 parts of phthalic acid diester, 1 part of the colorant, 0.5 parts of the ultraviolet stabilizer, and 0.5 parts of the antioxidant.

In a second possible implementation, the thermoplastic material includes the following components in parts by weight: 15-30 parts of a SEBS, 20-40 parts of a paraffin oil, 15-30 parts of polypropylene, 15-30 parts of calcium carbonate, and 0-3 parts of an auxiliary material. That is, the thermoplastic material is the TPES. The auxiliary material is at least one of an antioxidant, a lubricant, and a light stabilizer. In a specific embodiment, the TPES includes the following components in parts by weight: 25.5 parts of the SEBS, 30 parts of the paraffin oil, 22 parts of the polypropylene, 21 parts of the calcium carbonate, and 1.5 parts of the antioxidant.

In a third possible implementation, the thermoplastic material includes the following components in parts by weight: 95-99.5 parts of 1,4-Benzenedicarboxylic acid dimethyl ester polymer with 1,4-butanediol and α-hydro-ω-hydroxypoly(oxy-1,4-butanediyl), and 0.5-2 parts of an adhesive. That is, the thermoplastic material is the TPEE. The adhesive includes an acrylic adhesive, a rubber adhesive, a silicone adhesive, a carbamate adhesive, and an epoxy adhesive. In a specific example, the TPEE includes the following components in parts by weight: 99 parts of the 1,4-Benzenedicarboxylic acid dimethyl ester polymer with 1,4-butanediol and α-hydro-ω-hydroxypoly(oxy-1,4-butanediyl), and 1 part of the adhesive.

In a fourth possible implementation, the thermoplastic material includes the following components in parts by weight: 95-99.8 parts of a polymer of diphenyl isophthalate, 1,4-butanediol, terephthalic acid and poly(1,4-butanediol), and 0.1-2 parts of an adhesive. That is, the thermoplastic material is the TPEE. In a specific example, the TPEE includes the following components in parts by weight: 99.5 parts of the polymer of the diphenyl isophthalate, the 1,4-butanediol, the terephthalic acid and the poly(1,4-butanediol), and 0.5 part of the adhesive.

Optionally, the TPEE includes at least one of SK SKYPEL G130D, SK SKYPEL G140D, SK SKYPEL G155D and SK SKYPEL G163D. The SK SKYPEL G130D mainly includes the 1,4-Benzenedicarboxylic acid dimethyl ester polymer with 1,4-butanediol and α-hydro-ω-hydroxypoly (oxy-1,4-butanediyl). The SK SKYPEL G140D mainly includes the polymer of the diphenyl isophthalate, the 1,4-butanediol, the terephthalic acid and the poly(1,4-butanediol). SKYPEL serves as a product name registered by the SK Chemicals for the engineering thermoplastic elastomers. The engineering thermoplastic elastomers are the TPEE, with similar flexibility and elastic restoring force as rubber, and better mechanical strength, heat resistance and weather resistance than the rubber. Without vulcanization, the TPEE is the same as common thermoplastic resin. Resin with an easy molding processability is used to form the multifunctional flexible and mechanical material in a common polyester synthesizing method by adjusting a copolymer amount on a soft segment. The TPEE is copolymerized by 1,4-butanediol terephthalate and polybutanol. The TPEE can improve a physical rigidity and a chemical stability by increasing a proportion of a hard segment, and can improve a flexibility and a low-temperature property by increasing a proportion of a soft segment.

The G130D and the G140D have similar flexibility, elasticity and mechanical strength as the rubber, with better heat resistance and weather resistance than the rubber. The SKYPEL at all levels is a block copolymer, and includes a polybutylene terephthalate hard (crystalline) segment and a long chain based polyether glycol soft (noncrystalline) segment. Its attribute depends on a ratio of the hard segment to the soft segment.

Embodiments: Materials Used in the Embodiments and their Hardnesses are Listed in Table 1

TABLE 1

| No. | Type | Manufacturer | Shore hardness |
|---|---|---|---|
| Embodiment 1 | TPU1070A | Bayer of Germany | 70 A |
| Embodiment 2 | TPE06751 | DuPont of USA | 75 A |
| Embodiment 3 | HY3078 | DuPont of USA | 80 A |
| Embodiment 4 | HY4056 | DuPont of USA | 87 A |
| Embodiment 5 | G130D | SK of Korea | 80 A |
| Embodiment 6 | G140D | SK of Korea | 90 A |

The material in Embodiment 2 includes the following components in parts by weight: 20.5 parts of a SEBS (the CAS is 66070-58-4), 36 parts of a paraffin oil, 21 parts of polypropylene, 21 parts of calcium carbonate, and 1.5 parts of an antioxidant.

The material in Embodiment 5 includes the following components in parts by weight: 99.5 parts of 1,4-Benzenedicarboxylic acid dimethyl ester polymer with 1,4-butanediol and α-hydro-ω-hydroxypoly(oxy-1,4-butanediyl) (the CAS is 9078-71-1), and 0.5 part of an adhesive.

The material in Embodiment 6 includes the following components in parts by weight: 99 parts of a polymer of diphenyl isophthalate, 1,4-butanediol, terephthalic acid and poly(1,4-butanediol) (the CAS is 9086-55-9), and 1 part of an adhesive.

Test results in the embodiments show that if the material has the smaller hardness, the molded product is bent easily and has a smaller loading capability. By controlling the shore hardness of the material at 65 A, the molded product does not cause deformation easily, has a large loading capability, and meets a scenario with a large application amount and a high loading requirement.

It should be noted that those of ordinary skill in the art can further make variations and improvements without departing from the conception of the present disclosure. These variations and improvements all fall within the protection scope of the present disclosure. Therefore, the protection scope of this application shall be subject to the appended claims.

What is claimed is:

1. An applicator, configured to apply a cosmetic, a skin care product and/or a medicine to a hairless skin, and comprising a mounting portion and an application portion fixedly connected to the mounting portion, wherein at least two flocks are provided on the application portion; the mounting portion, the application portion and the at least two flocks are an integrally injection-molded piece made of a thermoplastic material; a shore hardness of the thermoplastic material is greater than 65 A; wherein the application portion includes a first surface and a second surface opposite each other, wherein both the first surface and the second surface are provided with the at least two flocks, and wherein each of the first surface and the second surface is a planar surface, a convex surface, or a concave surface; and wherein a density of the at least two flocks on the application portion is 10 pieces/mm$^2$ to 20 pieces/mm$^2$.

2. The applicator according to claim 1, wherein the shore hardness of the thermoplastic material is 70 A to 95 A.

3. The applicator according to claim 1, wherein the shore hardness of the thermoplastic material is 70 A, 72 A, 75 A, 80 A, 85 A, 87 A or 90 A.

4. The applicator according to claim 1, wherein a first end of each of the at least two flocks is fixedly connected to the application portion, and a second end of each of the at least two flocks is a free end; the second end of each of the at least two flocks extends toward an outer side of the application portion; each of the at least two flocks has an average diameter of 0.06 mm to 0.2 mm; and each of the at least two flocks has a length L of 0.6 mm to 2 mm.

5. The applicator according to claim 1, wherein a distance H between two adjacent flocks of the at least two flocks is identical.

6. The applicator according to claim 1, wherein a distance H between two adjacent flocks of the at least two flocks is 0.1 mm to 0.6 mm.

7. The applicator according to claim 1, wherein each of the at least two flocks is spatially shaped as a designated cone; the designated cone is a circular cone or a truncated cone; and the designated cone has a conicity of 1:15 to 1:20.

8. The applicator according to claim 7, wherein the thermoplastic material comprises the following components in parts by weight: 20-40 parts of polyurethane (PU), 20-30 parts of a polyester fiber, 20-30 parts of a filler, 15-25 parts of a plasticizer, 0-5 parts of a colorant, 0-1 parts of an ultraviolet stabilizer, and 0-1 parts of an antioxidant.

9. The applicator according to claim 7, wherein the thermoplastic material comprises the following components in parts by weight: 15-30 parts of a styrene-ethylene-butylene-styrene block copolymer (SEBS), 20-40 parts of a paraffin oil, 15-30 parts of polypropylene, 15-30 parts of calcium carbonate, and 0-3 parts of an auxiliary material.

10. The applicator according to claim 7, wherein the thermoplastic material comprises the following components in parts by weight: 95-99.5 parts of 1,4-Benzenedicarboxylic acid dimethyl ester polymer with 1,4-butanediol and α-hydro-ω-hydroxypoly(oxy-1,4-butanediyl), and 0.5-2 parts of an adhesive.

11. The applicator according to claim 7, wherein the thermoplastic material comprises the following components in parts by weight: 95-99.8 parts of a polymer of diphenyl isophthalate, 1,4-butanediol, terephthalic acid and poly(1,4-butanediol), and 0.1-2 parts of an adhesive.

12. The applicator according to claim 2, wherein each of the at least two flocks is spatially shaped as a designated cone; the designated cone is a circular cone or a truncated cone; and the designated cone has a conicity of 1:15 to 1:20.

13. The applicator according to claim 3, wherein each of the at least two flocks is spatially shaped as a designated cone; the designated cone is a circular cone or a truncated cone; and the designated cone has a conicity of 1:15 to 1:20.

14. The applicator according to claim 4, wherein each of the at least two flocks is spatially shaped as a designated cone; the designated cone is a circular cone or a truncated cone; and the designated cone has a conicity of 1:15 to 1:20.

15. The applicator according to claim 5, wherein each of the at least two flocks is spatially shaped as a designated cone; the designated cone is a circular cone or a truncated cone; and the designated cone has a conicity of 1:15 to 1:20.

16. The applicator according to claim 6, wherein each of the at least two flocks is spatially shaped as a designated cone; the designated cone is a circular cone or a truncated cone; and the designated cone has a conicity of 1:15 to 1:20.

* * * * *